(12) United States Patent
Weiss et al.

(10) Patent No.: US 8,509,915 B2
(45) Date of Patent: Aug. 13, 2013

(54) IMPLANTABLE ELECTRODE LINE DEVICE FOR REDUCING UNDESIRABLE EFFECTS OF ELECTROMAGNETIC FIELDS

(75) Inventors: Ingo Weiss, Berlin (DE); Stefan Knorr, Berlin (DE); Michelle Maxfield, Berlin (DE); Michael Friedrich, Kleinmachnow (DE)

(73) Assignee: Biotronik SE & Co. KG, Berlin (DE)

( * ) Notice: Subject to any disclaimer, the term of this patent is extended or adjusted under 35 U.S.C. 154(b) by 24 days.

(21) Appl. No.: 13/304,882

(22) Filed: Nov. 28, 2011

(65) Prior Publication Data

US 2012/0157808 A1  Jun. 21, 2012

Related U.S. Application Data

(60) Provisional application No. 61/424,079, filed on Dec. 17, 2010.

(51) Int. Cl.
*A61N 1/05* (2006.01)

(52) U.S. Cl.
USPC ............. 607/116; 607/63; 607/122; 600/411; 128/901

(58) Field of Classification Search
None
See application file for complete search history.

(56) References Cited

U.S. PATENT DOCUMENTS

| | | | |
|---|---|---|---|
| 5,687,735 A * | 11/1997 | Forbes et al. | 600/509 |
| 6,584,351 B1 * | 6/2003 | Ekwall | 607/9 |
| 7,013,180 B2 * | 3/2006 | Villaseca et al. | 607/116 |
| 8,032,228 B2 * | 10/2011 | Ameri et al. | 607/62 |
| 8,239,040 B2 * | 8/2012 | Geistert | 607/116 |
| 8,244,346 B2 * | 8/2012 | Foster et al. | 607/2 |
| 8,364,283 B2 * | 1/2013 | Halperin et al. | 607/116 |
| 8,369,964 B2 * | 2/2013 | Ameri | 607/116 |
| 2008/0049376 A1 * | 2/2008 | Stevenson et al. | 361/302 |
| 2008/0132985 A1 | 6/2008 | Wedan et al. | |
| 2009/0099555 A1 | 4/2009 | Viohl et al. | |
| 2009/0270956 A1 * | 10/2009 | Vase et al. | 607/116 |
| 2010/0228331 A1 * | 9/2010 | Conger | 607/122 |
| 2011/0029054 A1 * | 2/2011 | Tranchina | 607/116 |
| 2011/0196461 A1 * | 8/2011 | Weiss et al. | 607/116 |
| 2011/0208280 A1 * | 8/2011 | Li et al. | 607/115 |

(Continued)

FOREIGN PATENT DOCUMENTS

| | | |
|---|---|---|
| WO | 2007/047966 | 4/2007 |
| WO | 2008/115426 | 9/2008 |

OTHER PUBLICATIONS

European Search Report dated Apr. 5, 2013, 5 pages.

*Primary Examiner* — Kennedy Schaetzle
(74) *Attorney, Agent, or Firm* — ARC IP Law, PC; Joseph J. Mayo

(57) ABSTRACT

Implantable medical device having elongated electric line(s) with function conductors, which are respectively multi-stranded and connected to respective function electrode pole(s) to deliver treatment/record diagnostic signals, wherein a first function conductor has a first strand, which, in the course of the longitudinal extension of the first function conductor in first longitudinal section(s) has a first coupling with a second function conductor suitable for coupling electromagnetic radio-frequency waves guided in the second function conductor at least in part in the first strand(s) of the first function conductor, and wherein the first strand(s) in the course of the longitudinal extension of the first function conductor in second longitudinal section(s) has a second coupling with second strand(s) of the first function conductor, suitable for coupling electromagnetic radio-frequency waves guided in the at least one first strand at least in part in the at least one second strand of the first function conductor.

13 Claims, 5 Drawing Sheets

(56) References Cited

U.S. PATENT DOCUMENTS

2011/0270362 A1* 11/2011 Goedeke et al. ............... 607/63
2011/0288403 A1* 11/2011 Kondabatni et al. .......... 600/421
2012/0221086 A1* 8/2012 Wang ........................... 607/116
2012/0253340 A1* 10/2012 Stevenson et al. .............. 606/33

* cited by examiner

FIG. 2 - Prior Art -

IMPLANTABLE ELECTRODE LINE DEVICE FOR REDUCING UNDESIRABLE EFFECTS OF ELECTROMAGNETIC FIELDS

This application claims the benefit of U.S. Provisional Patent Application 61/424,079 filed on 17 Dec. 2010, the specification of which is hereby incorporated herein by reference.

BACKGROUND OF THE INVENTION

1. Field of the Invention

Embodiments of the invention relate to a permanently or temporarily implantable device having an elongated electric conductor.

2. Description of the Related Art

Devices of this type, for example, electrode lines for electrostimulation, have the disadvantage that the electric conductor thereof can heat up in an MRI scanner because the alternating magnetic fields prevailing in the MRI scanner induce not inconsiderable electric currents in the electric conductor. For this reason, nowadays patients with cardiac pace makers usually cannot be examined, or can be examined only to a limited extent, in an MRI scanner.

At least one stimulation electrode line is typically connected to implantable cardiac pace makers or defibrillators, which stimulation electrode line has a standardized electrical connection at its proximal end provided for connection to the cardiac pacemaker or defibrillator and has one or more electrode poles on its distal end provided for placement in the heart. An electrode pole of this type is used to deliver electrical pulses to the tissue (myocardium) of the heart or to sense electric fields in order to be able to sense an activity of the heart within the scope of the so-called sensing. Electrode poles are typically provided in the form of a ring around the electrode line with an electrically conducting surface or in the form of a point electrode or tip electrode at the distal end of the electrode line. The electrode poles are connected in an electrically conducting manner via one or more electric lines to contacts of the electrical connection of the electrode to contacts of the electric connection of the electrode line at the proximal end thereof. Thus one or more electric lines run between the contacts of the electrical connection the electrode lines at the proximal end thereof and the electrode poles at the distal end of the electrode lead, which electric lines electrically connect one or more of the electrode poles to one or more of the contacts. These electric lines can be used on the one hand to transmit stimulation pulses to the electrode poles or for transmitting electric signals recorded by means of the electrode poles to the proximal end of the electrode line and are referred to in the course of the further description as a function line. Function lines of this type are electric conductors necessary for the functions of the respective electrode line and as such are exposed to the risk of electric currents being induced in them through external alternating magnetic fields, which can lead, for example, to an undesirable heating up of the function lines or of the electrode poles connected to them.

BRIEF SUMMARY OF THE INVENTION

Embodiments of the invention are based on the object of creating a device that solves the problem described above.

According to one or more embodiments of the invention, this object is attained by a temporarily or permanently implantable medical device with at least one elongated electric line with at least two function conductors, which are respectively multi-stranded and of which each function conductor is connected to at least one respective function electrode pole to deliver treatment signals or to record diagnostic signals, in which a first of the function conductors has at least one first strand, which, in the course of the longitudinal extension of the first function conductor in at least one first longitudinal section, which forms only a partial section of the longitudinal extension of the function conductor, has a first coupling with a second of the function conductors, which coupling is configured to couple electromagnetic radio-frequency waves guided in the second function conductor at least in part in the at least one first strand of the first function conductor and not in at least one of the first different second strands of the first function conductor, and in which the at least one first strand in the course of the longitudinal extension of the first function conductor in at least one second longitudinal section different from the first longitudinal section has a second coupling with the at least one second strand of the first function conductor, which is suitable for coupling electromagnetic radio-frequency waves guided in the at least one first strand at least in part in the at least one second strand of the first function conductor.

In the medical device according to one or more embodiments of the invention, the at least one first strand of the first function conductor is exposed to a different electromagnetic influence of external fields from the at least one second strand of the same function conductor. Only the at least one first strand is exposed through the first coupling with a second function conductor to the electromagnetic effect of external fields to which the second function conductor is also subjected. Although the at least one second strand of the first function conductor is likewise subjected at any time to an electromagnetic effect of the respective external field, this effect differs due to the missing first coupling of the second strand(s) with the second function conductor and the inherent spatial separation of the second strand(s) from the second function conductor within the electric line. With induced high-frequency electromagnetic currents, this type of difference typically becomes noticeable by means of different phase positions.

The medical device of the one or more embodiments of the invention utilizes this, in that in at least parts destructive superposition of the electromagnetic waves guided in the at least one first strand and in the at least one second strand is created through the second coupling. Under the influence of a high-frequency alternating magnetic field, such as is used in magnetic resonance devices, this destructive superposition ensures a reduction of the high-frequency currents at the superposition location induced in the first function conductor. In this manner the first and the second coupling overall ensure a reduced current strength of induced high-frequency currents on the first function conductor. In the implanted condition of the medical device, this reduces or eliminates the undesirable heating of the body tissue that surrounds the function electrode connected to the first function conductor.

Exemplary embodiments of the medical device of the invention are explained below. The additional features of the individual exemplary embodiments can be combined with one another to form further embodiments of the medical device, unless they are explicitly described as mutually exclusive alternatives.

In preferred exemplary embodiments, the elongated electric line is a temporarily or permanently implantable electrode line for connecting one or more function electrode poles to a control device, such as, for example, the control device of an implantable cardiac pacemaker or an implantable defibrillator. However, the elongated line already per se forms a medical device for the purposes of the present specification.

In one embodiment, the at least one first strand of the first function conductor is guided in the first longitudinal section at a smaller spacing, suitable for producing the first coupling, from the second function conductor than outside the first longitudinal section of the first function conductor. The design of the geometries and dimensioning of the conductor spacings (in particular the establishment of the respective "proximity") is preferably carried out such that a minimization of the heating of the electrode poles is achieved during the operation of this implant in an environment loaded by alternating magnetic fields.

The first and the second coupling are preferably configured such that they cause an at least partially destructive interference of electromagnetic radio-frequency waves at the function electrode pole connected to the first function conductor, which electromagnetic radio-frequency waves are guided in the at least one first strand and the at least one second strand of the first function conductor. In other words, the second longitudinal section referenced above, in which the second coupling is present, can be at the location of the function electrode pole. At the function electrode pole a reduction of induced high-frequency currents as defined by one or more embodiments of the invention is particularly effective, because there is a particularly strong thermal coupling with the body tissues there in the implanted condition of the electric conductor.

It has proven to be advantageous if the at least one first strand and the at least one second strand of the first function conductor in at least one third longitudinal section, different from the first and second and arranged at a smaller spacing then these from a proximal end of the electric line, have a third coupling that is suitable for coupling electromagnetic radio-frequency waves guided in the at least one second strand at least in part in the at least one first strand of the first function conductor. The additional coupling in the third longitudinal section, which can be in particular a proximal coupling point, creates an electrical reference point there. In other words, through the provision of this additional coupling point, a reflection of the electromagnetic waves running on the at least one first strand of the function conductor is adjusted such that they have on the second longitudinal section of the function conductor such an amplitude position and phase position that can produce the desired cancellation effect particularly well.

Alternatively, a cross coupling can be provided for this purpose. This means that the at least one first strand and at least one strand of the second function conductor in at least one third longitudinal section, different from the first and the second and arranged at a smaller distance than these from a proximal end of the electric line, have a third coupling that is suitable for coupling electromagnetic radio-frequency waves guided in the at least one strand of the second function conductor at least in part into the at least one first strand of the first function conductor.

Different forms of a coupling with a phase shifter component can be achieved in different embodiments of the medical device. To this end, the at least one first strand of the first function conductor or the at least one second strand in the electric line is guided to at least one phase shifter component that is arranged upstream of the electrode pole. The phase shifter component is used, with preferably passive components, to adjust the phase position of the electromagnetic wave coupled into the first strand such that an interference as destructive as possible can be achieved at the location of the electrode pole.

In a variant of this embodiment, the connection of the at least one first strand of the first function line to the electrode poles and/or a proximally provided plug connector for connection to a control device is not carried out galvanically, but is realized via respectively one first phase shifter circuit. This circuit is preferably embodied exclusively with passive, that is, in particular resistive, inductive and or capacitive components, or uses suitably formed materials, which produce the effect of these passive components.

Alternatively or additionally, the corresponding connection of the at least one second strand of the first function line is connected to the function electrode pole and/to a plug connector with a corresponding second phase shifter circuit, for the embodiment of which the same applies as used in the last paragraph to describe the first phase shifter circuit. If both strands are fed to a respective phase shifter circuit, the superposition of the signals on the first and second strand can be mixed in a weighted manner in order to be able to adjust the cancellation as precisely as possible.

A phase shifter circuit of this type can be configured in a further development of this variant to additionally exert an attenuating effect on the electromagnetic waves.

Additionally or alternatively to passive components, active components such as switches, for example, realized as semiconductor components, can also be used in a phase shifter circuit of this type.

A particularly simple realization of the phase shifter circuit is formed by a dipole of an impedance Z, which is connected in series with the respective strand. For example, the coupling of the at least one first and the at least one second strand is capacitive. This can be realized through an insulation of one of the strands. Preferably, the capacity is greater than 1 picofarad.

The establishment of the couplings is favorable in terms of production technology if the first strands of the first function line, no matter how it is realized, whether, for example, as a helix or as a cable, is embodied in the same manner as that of the second feeder line, so that they can be guided close together (e.g., coiled parallel) in a simple manner to produce the respective coupling in the first, second and optionally third longitudinal sections.

The coupling of the at least one first and the at least one second strand is carried out in another exemplary embodiment by an electric sliding contact. A sliding contact as a mechanical embodiment of the contact can be embodied in a mobile manner, that is, rotatable, slidable and/or rotatable with feed, which promotes the mechanical flexibility of the electric conductor as a whole.

The at least one first strand of the first function conductor can be twisted with at least one strand of the second function conductor to produce the first coupling.

In another embodiment, the strands are embodied respectively as helices. In a variant of this embodiment, to produce the first coupling the at least one first strand of the first function conductor is wound in a helical manner around at least one strand of the second function conductor and envelops it.

It is also possible to embody one of the strands as a helix and the other strand at least in some sections as a cable, and to guide the cable-shaped helix to produce the coupling in the hollow space of the helix.

What has been said above for the first or second coupling can be easily applied to respectively the other referenced couplings, that is, the second or the first and the third coupling.

In preferred embodiments of the medical device, the at least one first strand of the first function conductor is an additional strand, which is not connected to a function electrode pole, while the at least one second strand of the first function conductor is a main strand that is connected to the function electrode pole which is assigned to the first function conductor.

The at least one first strand of the first function conductor and at least one strand of the second function conductor are produced from different materials in one embodiment. Cobalt-free materials, such as zirconium, tantalum, DFT or MP35N, for example, are suitable as materials.

In addition to the embodiments described herein other alternative embodiments may include some or all of the disclosed features.

BRIEF DESCRIPTION OF THE DRAWINGS

Further exemplary embodiments of the medical device are explained below based on the figures. They show.

DETAILED DESCRIPTION OF THE INVENTION

Figure 1:
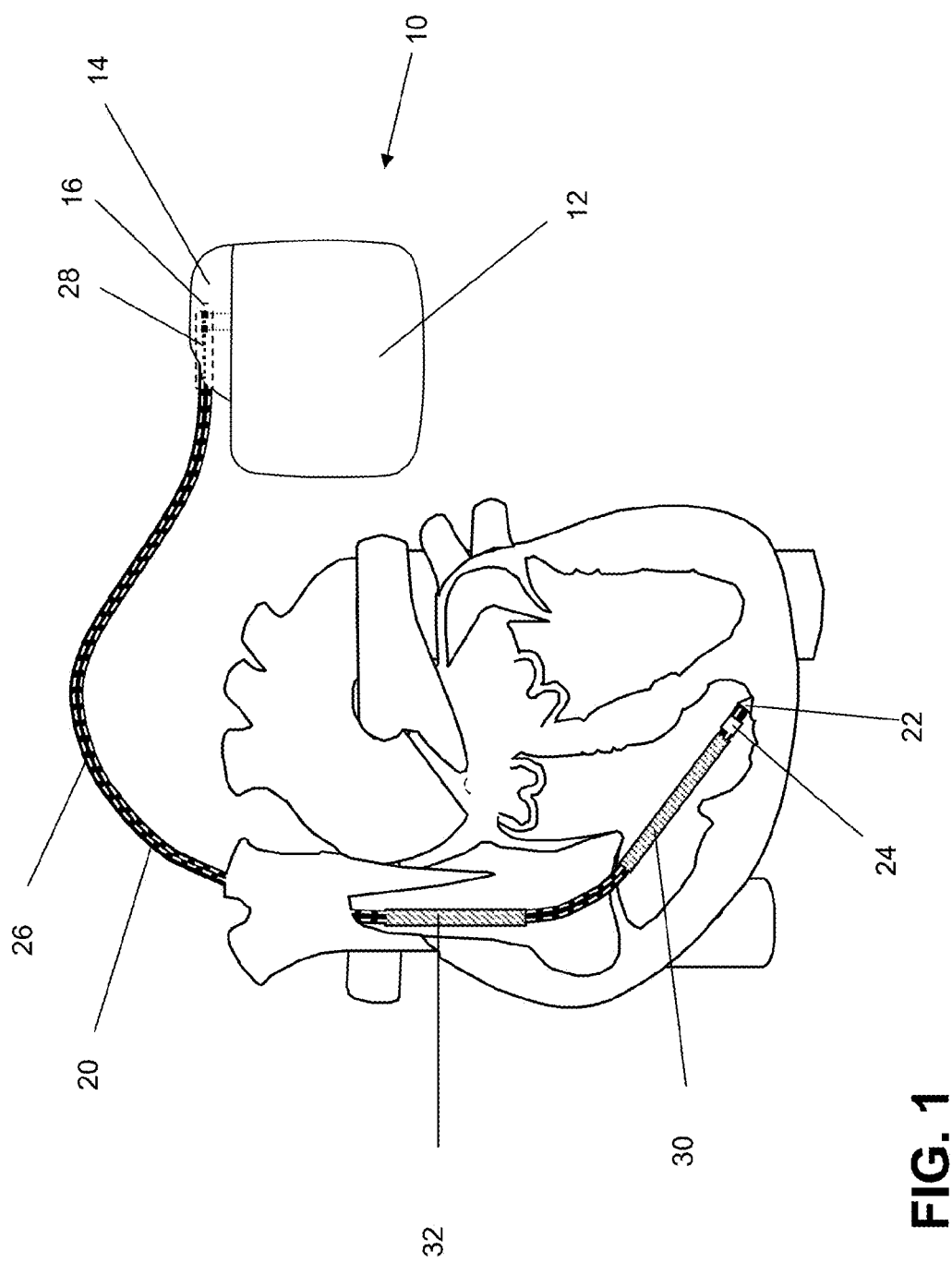
FIG. 1 Exemplary embodiments of medical devices in the form of a cardiac pacemaker and an electrode line connected thereto.

FIG. 1 shows an implantable cardiac stimulator 10 and an implantable electrode line 20 connected thereto as examples of implantable medical devices.

The implantable cardiac stimulator 10 can be a cardiac pacemaker or a cardioverter/defibrillator (ICD). In the exemplary embodiment shown, the cardiac stimulator 10 is a ventricular cardiac pacemaker and defibrillator. Other known cardiac stimulators are dual-chamber cardiac pacemakers for the stimulation of the right atrium and of the right ventricle or biventricular cardiac pacemakers, which can also stimulate the left ventricle in addition to the right ventricle.

Stimulators of this type typically have a housing 12, which is generally composed of metal and thus is electrically conductive and can be used as large-area electrode pole. A terminal housing 14 is typically attached to the outside of the housing 12, which terminal housing is also referred to as a header A header of this type typically has female contacts to accommodate plug contacts. The female contacts have electrical contacts 16 that are connected via corresponding conductors to an electronic system arranged in the housing 12 of the cardiac stimulator 10.

For the purposes of one or more embodiments of this invention, the electrode line 20 likewise represents an implantable medical device. Electrode poles in the form of a point electrode or tip electrode 22 and an annular electrode 24 arranged in their vicinity are arranged in a manner known per se at the distal end of the electrode line 20. The electrode poles 22 and 24 are embodied such that, depending on the function of a cardiac stimulator to which the electrode line 20 is connected, they are used to sense electrical potentials of the cardiac tissue (myocardium) or are embodied to emit electrical signals, for example, to deliver stimulation pulses to the cardiac tissue surrounding them. FIG. 1 shows how the electrode poles, that is, the tip electrode 22 and the annular electrode 24, in case of use the electrode line 20, are located in the apex of a right ventricle of a heart.

The tip electrode 22 as well as the annular electrode 24 is electrically connected via respectively at least one electric conductor 26 to a plug contact 28 at the proximal end of the electrode line 20. The plug contact 28 has electrical contacts that correspond to the electrical contacts 16 of the female contact in the terminal housing 14 of the implantable cardiac stimulator.

As is explained in more detail below, the electric conductors 26 can be embodied in the electrode line 20 in different longitudinal sections as approximately elongated cable pull conductors or as helically coiled conductors. Conductors of this type, which connect functional electrode poles to electrical contacts of the plug contact at the proximal end of the electrode line 20 in an electrically conductive manner, are also referred to as function conductors within the scope of this text, since they, for example, transmit electric signals for the purpose of treatment from the plug contact to the respective electrode pole or guide signals representing sensed electric potentials from the respective electrode pole to the plug contact and thus serve the elementary function of the medical device.

The electric function conductors 26, which connect the electrode poles 22 and 24 respectively to the electric contacts of the plug connector 28 of the electrode line 20, are surrounded by an insulating sheath over the major part of their length, so that an electric contact to the tissue of the heart is produced in targeted manner via the electrode poles.

In addition to the electrode poles 22 and 24, which are typically used for the (in this case ventricular) stimulation of the cardiac tissue, the electrode line 20 also has two larger-area electrode poles 30 and 32, which serve as defibrillation electrodes and are formed by at least one uninsulated helically coiled wire.

It should be pointed out that within the scope of this exemplary embodiment the invention is explained on the basis of a right ventricular cardiac pacemaker and defibrillator. However, an ablation electrode line can fundamentally also be used as a medical device for the purposes of the one or more embodiments of the invention, which ablation electrode line in the case of use likewise projects into the heart of a patient and which is controlled by a device arranged outside the patient and is connected thereto for this purpose. Furthermore, with adjustment according to usual practice in the field to the special requirements of the respective field of use, electrode lines of this type can also be used for the stimulation and dissipation of signals to nerves, the brain and other organs or for the feed of implantable sensors.

Some exemplary embodiments for the design according to one or more embodiments of the invention of the electrode line 20 are explained below. First, a design according to the prior art is discussed.

Figure 2:
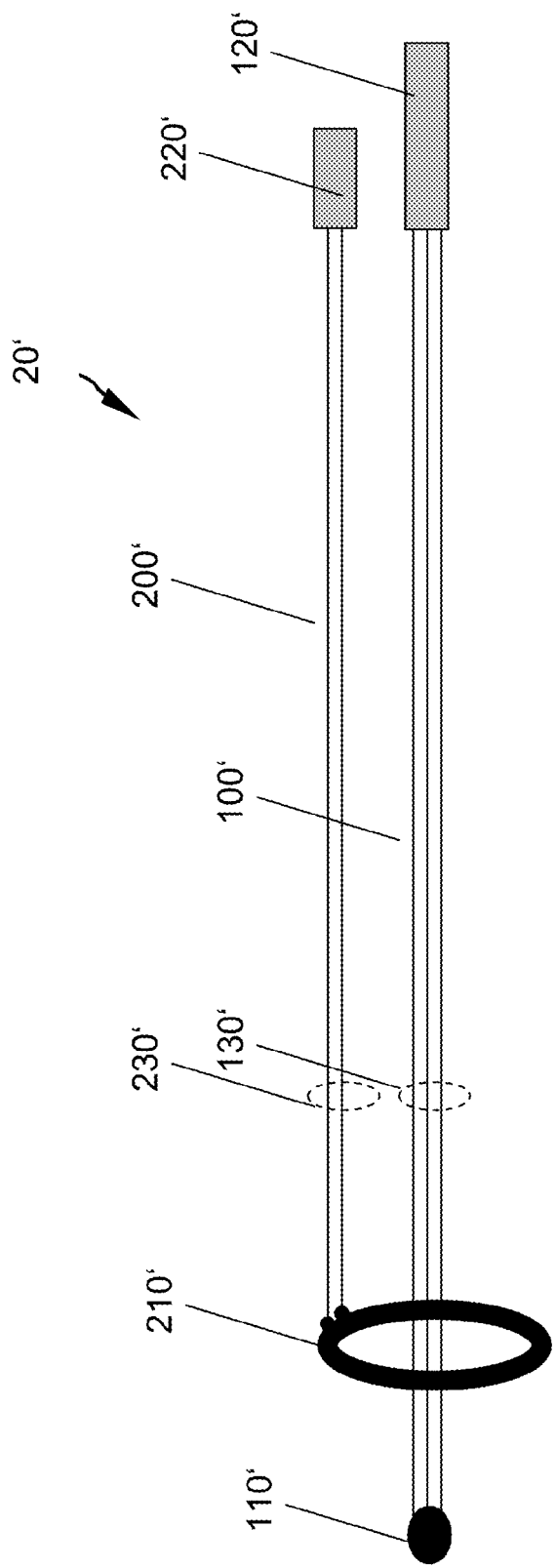
FIG. 2 A diagrammatic representation of an electrode line according to the prior art.

FIG. 2 shows a diagrammatic representation of an electrode line 20' according to the prior art. The electrode line has at its distal end two function electrode poles in the form of a tip electrode pole 110' and an annular electrode pole 210'. For the feed or dissipation of signals to or from the tip electrode pole 110', a function line 100' is connected to the tip electrode pole 110', which function line in the present example has 3 strands. Proximally it is connected to a plug connector pole 120', which can be connected to a control device of a cardiac pacemaker.

For the feed or dissipation of signals to or from the annular electrode pole 210', a function line 200' is connected to the annular electrode pole 210', which function line in the present example has 2 strands. Proximally, the function line 200' is connected to a plug connector pole 220', which likewise can be connected to the control device of the cardiac pacemaker. The strands of the function line 100' are guided close to one another, which is indicated by a dashed circle 130'. Likewise, the strands of the function line 200' are guided close to one another, which is indicated by a dashed circle 230'.

Figure 3:
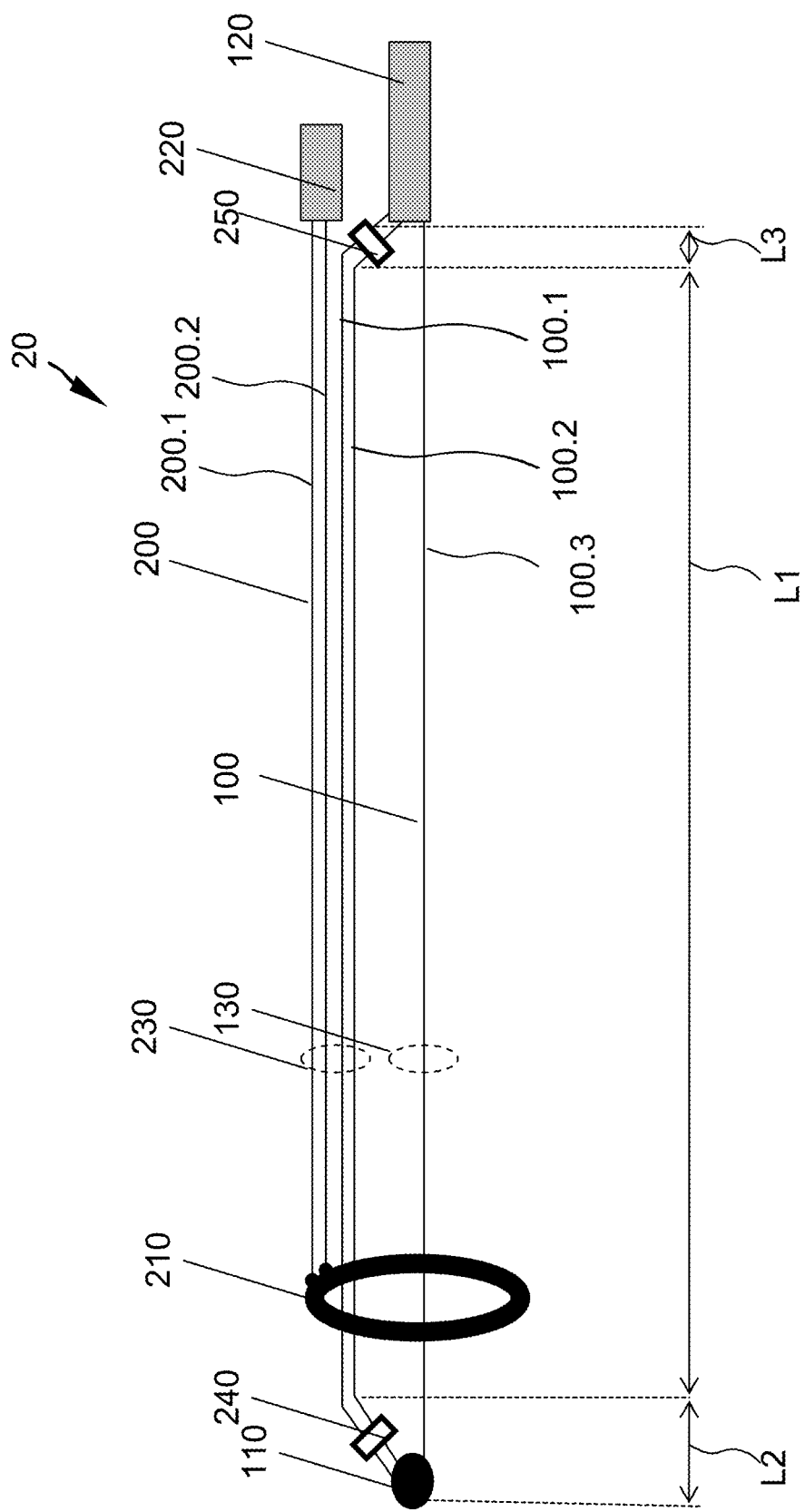
FIG. 3 A diagrammatic representation of an exemplary embodiment of an electrode line according to one or more embodiments of the invention.

FIG. 3 shows a correspondingly diagrammatic representation of an exemplary embodiment of an electrode line.

For the sake of the simplicity of the representation, here, as in the following figures, largely identical reference numbers are used for structural elements corresponding to one another, apart from the prime sign used at the end of the reference numbers, which is omitted in FIGS. 3 through 5 to characterize the difference between the prior art and exemplary embodiments of the invention.

The exemplary embodiments described here are based in some features on the known embodiment for the sake of the simplicity of the representation. However, this is done only to clarify the difference of the embodiments according to the invention, and is not intended to mean that such features are necessary for realizing an embodiment of the invention. For example, FIGS. 3 through 5 take over the number of strands of the function conductors 100 and 200 from the example of FIG. 2. However, the actual number of strands can also be higher than the number shown. The function conductor 100, for example, can also have only 2 strands. In principle, embodiments of the invention can even be realized with respectively one strand per function conductor.

The following description concentrates on differences of the electrode line of the present exemplary embodiments compared to the known embodiment of FIG. 2.

Of the three strands 100.1 through 100.3 of the first function conductor 100, in the present exemplary embodiment the strands 100.1 and 100.2 as first strands for the purposes of the introductory description of an embodiment of the invention are guided at a distance from a first longitudinal section L1 by the strand 100.3, which for the purposes of the introductory description of an embodiment of the invention forms a second strand, wherein the strands of the function line 100.3 are guided distal to first strands 100.1 and 100.2 to form a spatial separation as indicated by a dashed circle 130. In this first longitudinal section, they are guided close to strands 200.1 and 200.2 of the second function line 200, whereby an inductive and capacitive coupling of electromagnetic radio-frequency waves from the second function line 200 into the two strands 100.1 and 100.2 is realized, as a first coupling 230 in terms of the above description.

The phases of coupled-in waves are shifted in a phase shifter 240 arranged near to the distal end of the first function conductor 100. This is carried out to achieve a destructive interference in the coupling of the waves guided on the strands 100.1 and 100.2 into the strand 100.3 by a second coupling in a second longitudinal section L2 on the tip electrode 110.

To form a phase reference, an additional phase shifter 250 is provided in a third proximal longitudinal section L3.

In the present medical device, the strands 100.1 and 100.2 of the first function conductor 100 are subjected to a different electromagnetic effect of external fields than the at least strand 100.3 of the same function conductor. Through the first coupling 230 with the second function conductor 200, only strands 100.1 and 100.2 are subjected to that electromagnetic effect of external fields to which the second function conductor 200 is also subjected. Although the strand 100.3 of the first function conductor 100 is likewise subjected at any time to an electromagnetic effect of the respective external alternating field, this effect differs due to the missing first coupling 230 of the strand 100.3 to the second function conductor 200 and the inherent spatial separation of the strand 100.3 from the second function conductor 200 inside the electric line 20. Differences of this type become noticeable with induced high-frequency electromagnetic currents by different phase positions, which are used for the destructive interference at the tip electrode pole 110.

Figure 4:
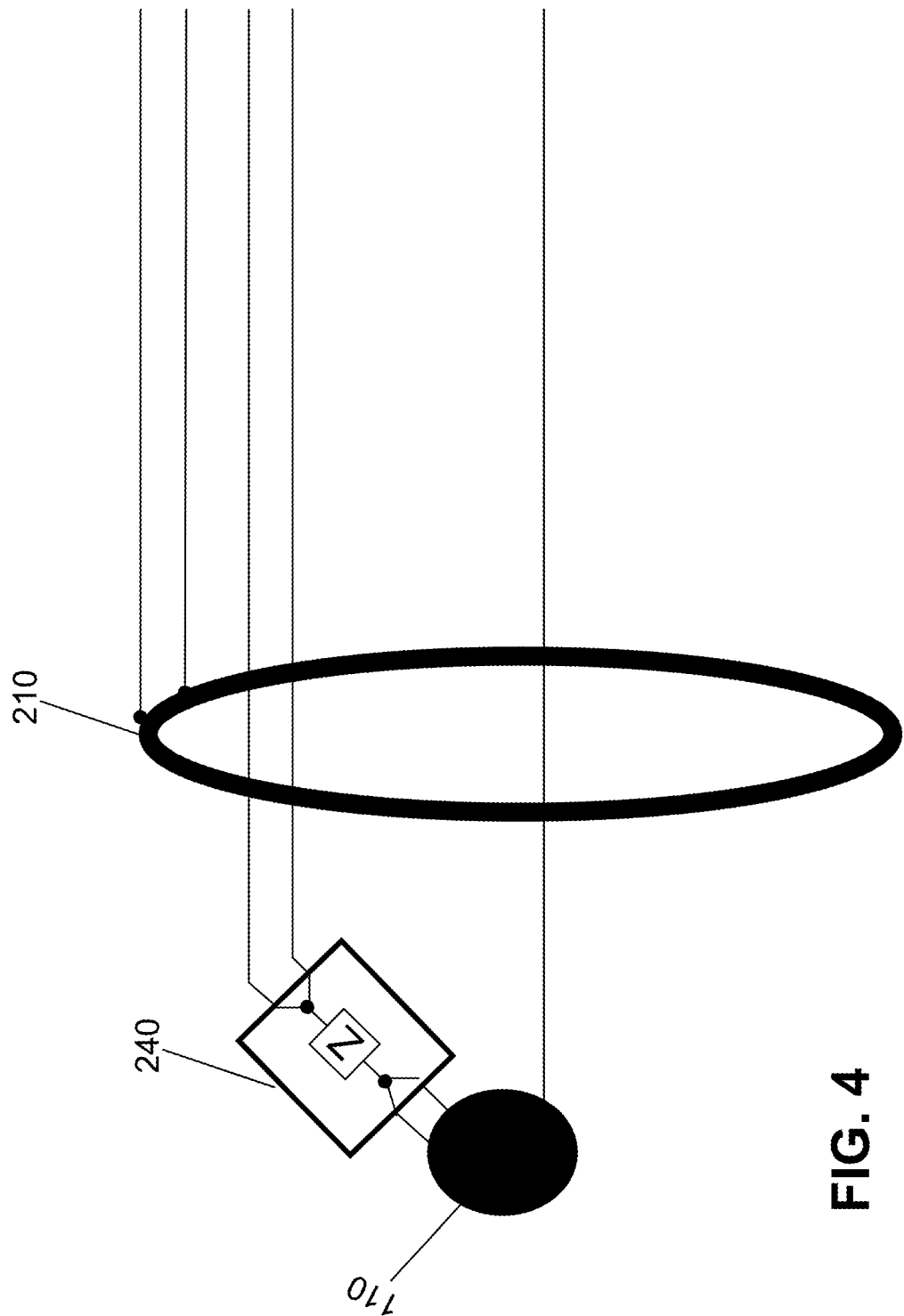
FIG. 4 A diagrammatic representation of a first variant of the exemplary embodiment of FIG. 3.

FIG. 4 shows a diagrammatic representation of a first variant of the exemplary embodiment of FIG. 3, in which the phase shifter 240 has a special characteristic of a dipole with an impedance Z, which is connected in series with the respective strands 100.1 and 100.2. The impedance Z can be, for example, a capacity greater than 1 picofarad. Alternative realizations of the phase shifter 240/250 have an impedance Z in the form of an ohmic resistance R where R<200 ohm or where R>1000 ohm, or at one end of the strands R<200 ohm and at the other end of the strands R>1000 ohm.

The phase shifter 240 or 250 can contain the impedance Z alternatively in the form of an LC circuit or in the form of an RLC. Here |Z|<200 ohm or |Z|>1000 ohm is realized in a frequency-dependent manner, for example, as a low pass, high pass, band pass, or band stop.

Figure 5:
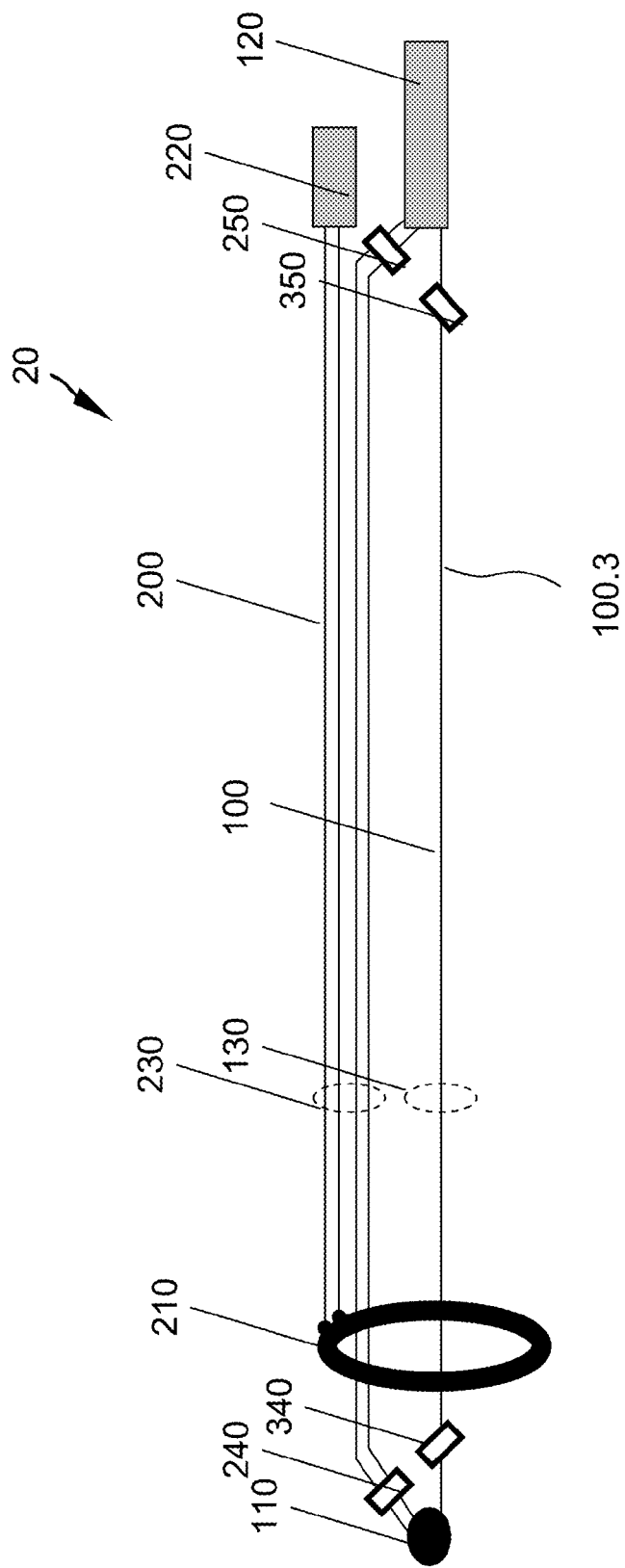
FIG. 5 A diagrammatic representation of a further exemplary embodiment of an electrode line according to one or more embodiments of the invention.

FIG. 5 is a diagrammatic representation of a further exemplary embodiment of an electrode line according to an embodiment of the invention. This variant differs from that of FIG. 3 only in that the strand 100.3 is also provided with phase shifters 340 and 350.

To improve the effect, the lumen of the sheath of the electrode line 20 can be filled with insulation material. The function conductors can be guided in the interior of the insulation material. The strands can then also be guided without an individual insulation in the electrode conductor. An additional inner insulation sheath can be omitted to save space.

With the helical guidance of the strands of the function conductors, a silicone filling can be used between the inner and outer helices. In addition, a silicone sheath can be used, which causes a good coupling of energy into the surrounding tissue.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. An implantable medical device comprising:
   at least one elongated electric line with at least two function conductors, which are respectively multi-stranded and of which each function conductor is connected to at least one respective function electrode pole to deliver treatment signals or to record diagnostic signals in a first function conductor (100) and a second function conductor (200);
   wherein said first function conductor of the at least two function conductors has at least one first strand (100.1,100.2), which, in a course of a longitudinal extension of the first function conductor in at least one first longitudinal section (L1), which forms only a partial section of the longitudinal extension of the first function conductor, has a first coupling (230) with the second function conductor (200) of the at least two function conductors, which coupling is configured to couple electromagnetic radio-frequency waves guided in the second function conductor at least in part in the at least one first strand (100.1,100.2) of the first function conductor and not in at least one of the second strand (100.3) of the first function conductor, and in which the at least one first strand (100.1,100.2) in the course of the longitudinal extension of the first function conductor (100) in at least one second longitudinal section (L2) different from the first longitudinal section (L1) has a second coupling with the at least one second strand (100.3) of the first function conductor (100), which is configured to couple electromagnetic radio-frequency waves guided in the at least one first strand at least in part in the at least one second strand of the first function conductor.

2. The implantable medical device according to claim 1, in which the at least one first strand of the first function conductor is guided in the at least one first longitudinal section at a smaller spacing, to produce the first coupling (230), from the second function conductor than outside the first longitudinal section (L1) of the first function conductor.

3. The implantable medical device according to claim 1, in which the first and the second coupling are configured to produce an at least partially destructive interference of said electromagnetic radio-frequency waves at the at least one respective function electrode pole, wherein said electromagnetic radio-frequency waves are guided in the at least one first strand and the at least one second strand of the first function conductor.

4. The implantable medical device according to claim 1, in which the at least one first strand and the at least one second strand of the first function conductor in at least one third longitudinal section, different from the first and second and arranged at a smaller spacing then these from a proximal end of the at least one elongated electric line, have a third coupling that is configured to couple electromagnetic radio-frequency waves guided in the at least one second strand at least in part in the at least one first strand of the first function conductor.

5. The implantable medical device according to claim 1, in which the at least one first strand and at least one strand of the second function conductor in at least one third longitudinal section, different from the first and the second and arranged at a smaller distance than these from a proximal end of the at least one elongated electric line, have a third coupling that is configured to couple electromagnetic radio-frequency waves guided in the at least one strand of the second function conductor at least in part into the at least one first strand of the first function conductor.

6. The implantable medical device according to claim 1, further comprising at least one phase shifter component that is arranged near the at least one respective function electrode pole wherein the at least one first strand of the first function conductor or the at least one second strand is guided in the at least one elongated electric line of the at least one phase shifter component.

7. The implantable medical device according to claim 1, further comprising an electric sliding contact where the coupling of the at least one first and the at least one second strand is carried out by the electric sliding contact.

8. The implantable medical device according to claim 1, in which the coupling of the at least one first and the at least one second strand is capacitive.

9. The implantable medical device according to claim 1, in which the at least one first strand of the first function conductor is an additional strand that is not connected to the at least one respective function electrode pole, and in which the at least one second strand of the first function conductor is a main strand that is connected to the at least one respective function electrode pole that is assigned to the first function conductor.

10. The implantable medical device according to claim 1, in which the at least one first strand of the first function conductor is twisted with at least one strand of the second function conductor.

11. The implantable medical device according to claim 1, in which the at least one first strand of the first function conductor is wound in a helical manner around at least one strand of the second function conductor and envelops around said second function conductor.

12. The implantable medical device according to claim 1, in which the at least one first strand of the first function conductor is configured at least in some sections as a cable line.

13. The implantable medical device according claim 1, in which the at least one first strand of the first function conductor and at least one strand of the second function conductor comprise different materials.

* * * * *